(12) United States Patent
Stimpson (10) Patent No.: US 11,457,830 B2
(45) Date of Patent: Oct. 4, 2022

(54) CATHETER ASSEMBLY

(71) Applicant: Laborie Medical Technologies Canada ULC, Mississauga (CA)

(72) Inventor: Philip G. Stimpson, West Palm Beach, FL (US)

(73) Assignee: Laborie Medical Technologies Canada ULC, Mississauga (CA)

(*) Notice: Subject to any disclaimer, the term of this patent is extended or adjusted under 35 U.S.C. 154(b) by 60 days.

(21) Appl. No.: 16/553,284

(22) Filed: Aug. 28, 2019

(65) Prior Publication Data

US 2020/0046237 A1 Feb. 13, 2020

Related U.S. Application Data

(62) Division of application No. 14/774,603, filed as application No. PCT/US2014/026271 on Mar. 13, 2014, now Pat. No. 10,433,741.

(60) Provisional application No. 61/867,395, filed on Aug. 19, 2013, provisional application No. 61/779,996, filed on Mar. 13, 2013.

(51) Int. Cl.
| | |
|---|---|
| *A61B 5/03* | (2006.01) |
| *A61M 25/00* | (2006.01) |
| *A61B 5/00* | (2006.01) |
| *A61B 5/20* | (2006.01) |

(52) U.S. Cl.
CPC ............ *A61B 5/036* (2013.01); *A61B 5/205* (2013.01); *A61B 5/6852* (2013.01); *A61B 5/6853* (2013.01); *A61M 25/0097* (2013.01); *A61B 2562/0247* (2013.01); *A61M 2025/0003* (2013.01)

(58) Field of Classification Search
None
See application file for complete search history.

(56) References Cited

U.S. PATENT DOCUMENTS

| | | | | |
|---|---|---|---|---|
| 4,679,567 A | * | 7/1987 | Hanlon | ............... G01L 19/0084 600/561 |
| 5,273,047 A | * | 12/1993 | Tripp | .................. A61B 5/0215 73/740 |
| 5,314,443 A | | 5/1994 | Rudnick | |

(Continued)

FOREIGN PATENT DOCUMENTS

| | | |
|---|---|---|
| EP | 2 101 159 A2 | 9/2009 |
| EP | 2494932 A2 | 9/2012 |

(Continued)

OTHER PUBLICATIONS

Partial European Search Report of the European Patent Office dated Feb. 15, 2017, in corresponding EP Application No. 14775663.9.

(Continued)

*Primary Examiner* — Benjamin S Melhus
(74) *Attorney, Agent, or Firm* — TraskBritt (57) ABSTRACT

A catheter hub assembly includes a body. A pressure sensor is disposed within the body to sense pressure within a catheter and communicating with the body. The body has a chamber formed therein having a predetermined volume. A stopper assembly, slideably moves to engage the body forming a gastight seal within the chamber for pushing a column of gas ahead of the stopper assembly as the stopper assembly moves from a first position to a second position.

3 Claims, 8 Drawing Sheets

(56) References Cited

U.S. PATENT DOCUMENTS

| | | | | |
|---|---|---|---|---|
| 5,522,266 | A | * | 6/1996 | Nicholson ............. G01L 9/0055 73/708 |
| 5,551,300 | A | * | 9/1996 | Vurek .................. A61B 5/0215 73/756 |
| 5,573,007 | A | | 11/1996 | Bobo, Sr. |
| 5,581,038 | A | * | 12/1996 | Lampropoulos ..... A61B 5/0215 73/721 |
| 6,210,375 | B1 | | 4/2001 | Moulton et al. |
| 7,976,475 | B2 | * | 7/2011 | Dijkman ............. A61B 5/0215 600/561 |
| 2003/0167022 | A1 | * | 9/2003 | Dijkman ............. A61B 5/0215 600/561 |
| 2005/0187430 | A1 | * | 8/2005 | Aundal ........... A61M 25/10188 600/31 |
| 2006/0116554 | A1 | * | 6/2006 | Dijkman ................ A61B 5/205 600/300 |
| 2007/0083088 | A1 | * | 4/2007 | Dijkman ............. A61B 5/0002 600/300 |
| 2007/0179400 | A1 | * | 8/2007 | Dijkman ................ A61B 5/036 600/561 |
| 2009/0069714 | A1 | * | 3/2009 | Eichmann ............. A61B 5/002 600/573 |
| 2009/0306539 | A1 | * | 12/2009 | Woodruff ............... A61B 5/205 600/561 |
| 2010/0094113 | A1 | | 4/2010 | Robinson et al. |
| 2010/0114063 | A1 | | 5/2010 | Recinella et al. |
| 2011/0295301 | A1 | | 12/2011 | Hoem et al. |
| 2012/0220984 | A1 | * | 8/2012 | Christensen .......... A61M 39/10 604/535 |
| 2013/0184612 | A1 | * | 7/2013 | Quackenbush ...... A61B 5/1076 600/587 |
| 2014/0107527 | A1 | * | 4/2014 | Dijkman ................ A61B 5/205 600/561 |

FOREIGN PATENT DOCUMENTS

| | | |
|---|---|---|
| JP | 2010115489 A | 5/2010 |
| JP | 2011244927 A | 12/2011 |
| KR | 20120086901 A | 8/2012 |
| RU | 2434579 C2 | 11/2011 |
| WO | 1999059467 A1 | 11/1999 |
| WO | 20070778455 A1 | 7/2007 |
| WO | 2010033468 A1 | 3/2010 |
| WO | 2010048638 A1 | 4/2010 |

OTHER PUBLICATIONS

Extended European Search Report of the European Patent Office dated May 19, 2017, in corresponding EP Application No. 14775663.9.

Office Action of the Japanese Patent Office dated Dec. 19, 2018, in corresponding Japanese Patent Application No. 2016-502089.

International Search Report for PCT/US2014/026271 dated Jul. 18, 2014.

International Search Report for PCT/US2014/026271 dated Sep. 15, 2015.

Russian Office Action of the Federal Institute of Intellectual Property in Moscow dated Sep. 14, 2017 in corresponding Russian Application No. 2015142456/14(065632).

Notice of Rejection filed on Jul. 31, 2020 in corresponding Korean Patent Application No. 10-2015-7028833 (translation included).

First Office Action dated Mar. 17, 2021 received in corresponding Chinese Patent Application No. 2019107399890.

\* cited by examiner

CATHETER ASSEMBLY

CROSS REFERENCE TO RELATED APPLICATIONS

This application is a Divisional of the U.S. Utility patent application Ser. No. 14/774,603, filed Sep. 10, 2015, now U.S. Pat. No. 10,433,741, issued Oct. 8, 2019, which is the national phase under 35 U.S.C. § 371 of PCT International Application No. PCT/US2014/026271, filed Mar. 13, 2014, which claims priority of U.S. Provisional Patent Application No. 61/867,395, filed Aug. 19, 2013, and U.S. Provisional Patent Application No. 61/779,996, filed Mar. 13, 2013.

BACKGROUND OF THE INVENTION

The present invention is directed to a pressure sensing catheter, and in particular, a catheter charger housing for use with a catheter.

Pressure sensing catheters are known in the art by way of example from U.S. Pat. No. 5,573,007 which describes a gas-column pressure measuring catheter for use intravenously or in a bladder to measure the pressure of the fluid in those body areas. The catheters have a gas-filled lumen communicating with a membrane-walled chamber on the catheter body. Pressure changes exerted against the outer surface of the membrane walled chamber result in the transmission of pressure changes through the gas-filled catheter lumen. The membrane walled chamber may be located on the side wall of the catheter body or at the distal end of the catheter body. A gas-column pressure measuring sensor is provided at a proximal end of the catheter through an electronic sensor. The air-column of the catheter is in direct fluid communication with the sensor.

Similar structures are known for liquid-filled catheters in which the pressure transmitting medium is a liquid of sufficient viscosity to allow transmittal of pressure waves from the chamber to the sensor.

Prior art gas catheters often require an electromechanical pump system or a syringe like structure to provide the desired degree of inflation to facilitate the intended pressure monitoring function of the catheter. The sensory circuitry is far removed from the pump injection structure resulting in a bulky hard to use device. This increases the amount of inventory on hand and the cost of manufacture. The catheter chargers and associated circuitry, the structure which sets the fluid pressure (pressure of the gas or liquid) within the lumen are sophisticated and complex requiring separate housing.

Accordingly, a catheter system which overcomes the shortcomings of the prior art is desired.

BRIEF SUMMARY OF THE INVENTION

A pressure monitoring system includes a catheter hub assembly having a body. A pressure sensor is disposed within the body to sense pressure within a catheter which communicates with the body. The body has a chamber formed therein which has a predetermined volume. A stopper assembly slidably moves through the chamber forming a gas tight seal within the chamber pushing a column of gas ahead of the stopper assembly as the stopper assembly moves from a first position to a second position.

In one embodiment, catheter hub assemblies may be gang mounted through an electronics assembly for catheters in which there is a housing. Circuitry is disposed within the housing. A connector having second circuitry which communicates with the first circuitry is disposed in the housing. A first catheter hub assembly and at least a second catheter hub assembly communicate with the second circuitry.

A catheter hub assembly includes a housing. A pressure sensor is disposed within the housing to sense a pressure of fluid within the housing. The catheter assembly terminates with, and is in fluid communication with the housing. A charger is disposed in the housing and moveable between a first position defining a volume of fluid within the housing and a second position charging the volume of fluid into the catheter assembly. The charger may be a screw moveable between a first position and second position within the housing.

In another preferred embodiment of the invention, the catheter hub assembly includes a housing, a pressure sensor is disposed within the housing to sense pressure within a catheter communicating with the housing. The housing has a chamber formed therein of a predetermined volume. A stopper assembly adapted to slideably move through the chamber and form a gas tight seal within the chamber pushes a column of gas ahead of the stopper assembly as it moves from a first position to a second position. The stopper includes a push-in stopper having a bore formed therein, a catheter is disposed within the bore and extends along a length of the stopper assembly. In an alternative embodiment, the catheter extends beyond the length of the stopper.

During use, the catheter and a catheter hub are connected to the sensor assembly. The lumen is charged to inflate the membrane forming a pressure chamber within the patient's body. Changes in pressure sensed at the pressure chamber allow expansion or contractions thereof which are translated as longitudinal waves along the lumen to the diaphragm. The sensor determines pressure changes sensed by the chamber.

BRIEF DESCRIPTION OF THE DRAWINGS

Other objects, features and advantages of the present invention will be apparent from the written description and the drawings in which.

DETAILED DESCRIPTION OF THE PREFERRED EMBODIMENT

Reference is first made to FIGS. 1-3 and 11 in which a pressure monitoring system, generally indicated as 10 is shown. Pressure monitoring system 10 includes, extending from the proximal end to the distal end, a sensor assembly 830 and a catheter sub-assembly 20. It should be noted, that given the nature of the drawings, distal end and proximal end are relative terms; the proximal end being that end of the structure in the drawing closest to sensor assembly 830 and the distal end being the end of the structure relatively farthest from sensor assembly 830.

Figure 1:
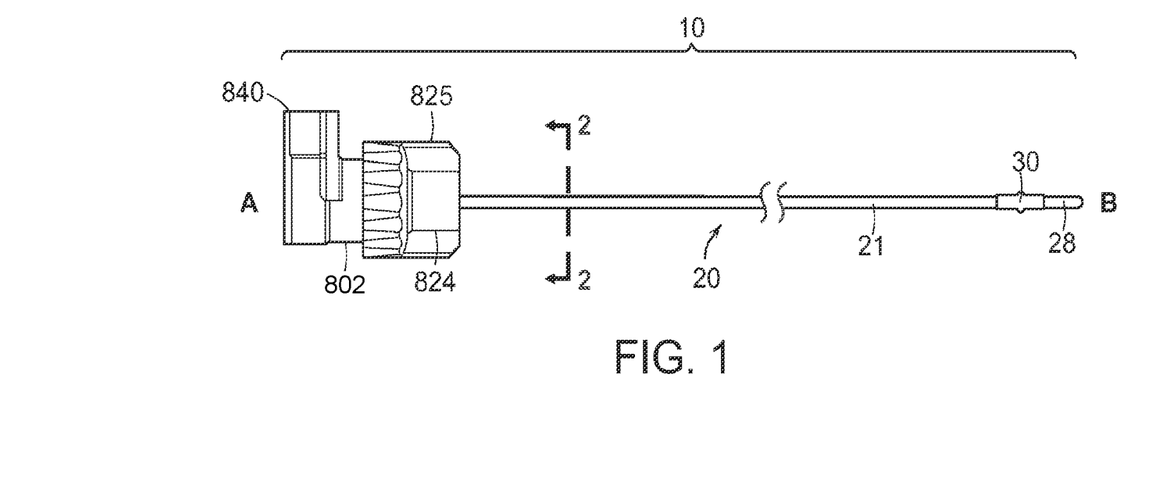
FIG. 1 is a plan view of a catheter system constructed in accordance with the invention.
Figure 2:
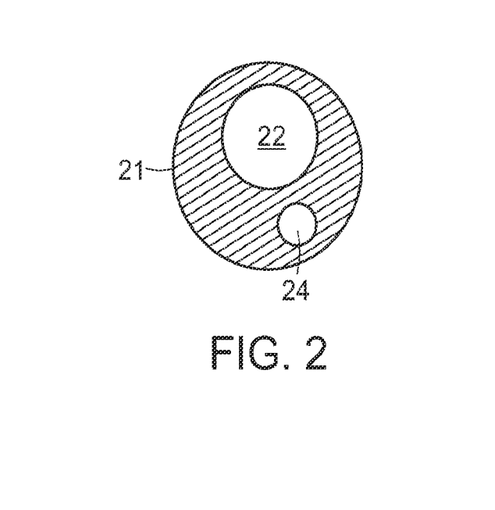
FIG. 2 is a sectional view taken along lines 2-2 of FIG. 1.
Figure 3:
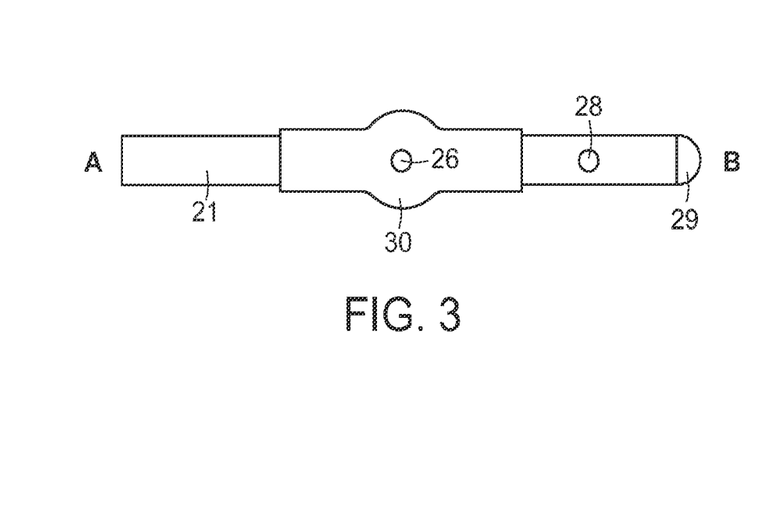
FIG. 3 is a plan view of the distal end of the catheter assembly showing the inflatable chamber constructed in accordance with the invention.

An expandable membrane 30 is disposed on an outer surface of catheter housing 21 across eye 26 to form an inflatable chamber in fluid communication with lumen 24. Membrane 30 may be formed as a sheet affixed with adhesive to an exterior wall of catheter housing 21, or in the alternative may be formed as a balloon that is heat shrunk about catheter housing 21 to form a tight friction fit. Membrane 30 may be formed of any inert expandable material approved for medical use. However, in a preferred embodiment, the membrane may be made from Polyethylene Terephthalate by way of non-limiting example.

A second eye 28 may also be formed at a portion of catheter housing 21 at the relatively distal end thereof. A second lumen 22 extends longitudinally through catheter housing 21 from a proximal end of catheter housing 21 to terminate and be in fluid communication with eye 28.

As will be discussed below, each lumen 22, 24 extends beyond catheter housing 21 at the proximal end thereof. Lumen 22 in one embodiment is an infusion lumen and therefore is not relied upon to provide a pressure sensing operation and terminates and is coupled to an operative device such as is described below to pump fluid such as air through eye 28 by way of lumen 22 as part of a pressure measuring procedure. In another embodiment, eye 28 may inflate a second balloon.

In an exemplary, but non-limiting embodiment, lumen 22 may be a vesicle (bladder) monitoring lumen. Catheter hub assembly 800 is affixed to lumen 24 and closes the catheter system 10 by sealing lumen 24.

In radio-opaque embodiments, the distal portion 29 of catheter housing 21 may be formed from a radio-opaque material such as a silver wire. In this way, a catheter assembly may be utilized for x-ray or other procedures. Pressure monitoring system 10 includes a pressure sensing assembly 830 for sensing movement at catheter sensing diaphragm to determine a pressure experienced at the chamber formed by membrane 30.

At the site of use, for example, at a clinic, doctor's office or hospital, if used in connection with the measurement of bladder pressure, the package is opened and inserted into the patient. Closed catheter system 10 is then coupled to pressure sensing assembly 830 to complete the fully assembled pressure monitoring system 800. When sensor sub-assembly 830 is coupled to body 802 which in turn is coupled to catheter stopper 824, environmental air is trapped between housing 802 and catheter stopper 824 creating air pressure within pressure sensing assembly 830. This air pressure is sufficient to inflate the chamber formed by membrane 30 a predetermined amount; charging/zeroing the lumen. Therefore, during use, the catheter is inserted into the bladder and body 802 is then attached to catheter stopper 824, so that inflation of the chamber happens in situ.

At this point, as is known in the art, the fluids within the bladder, by way of non-limiting example, exert a pressure on the chamber formed by membrane 30. If the net pressure is greater than that initially provided by inflating membrane 30 as discussed above, the chamber will shrink, the pressure will be transmitted as a longitudinal wave through the fluid column contained in lumen 24 to force air against a piezo- electric sensor 836 in the form, in one non-limiting embodiment, of transducers which converts the force of the air into an electrical signal corresponding to a pressure value. Conversely, if the pressure in the bladder is less than that in the chamber formed by membrane 30, the chamber will expand in the distal direction providing a negative force which is also sensed by piezo electric sensor 836.

Figure 4:
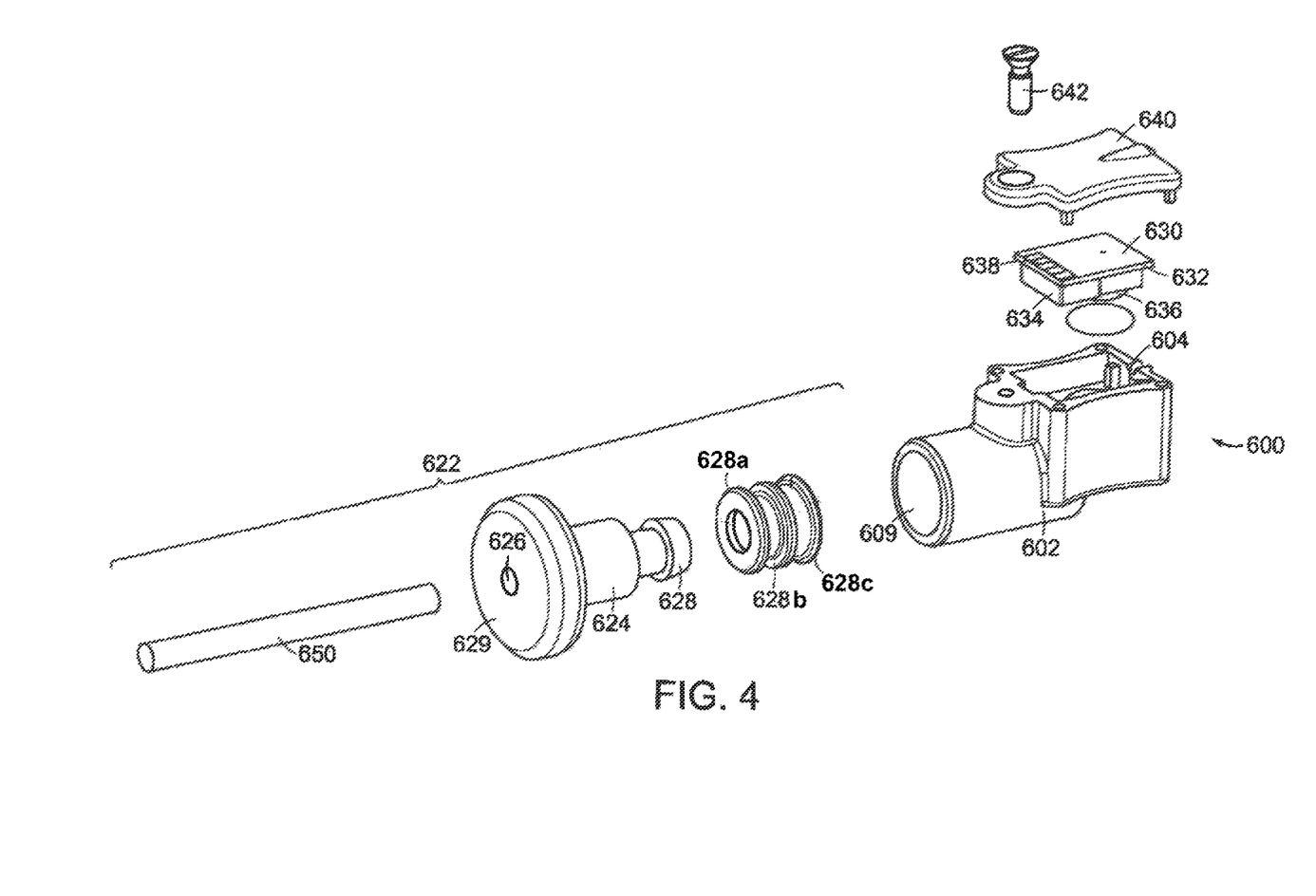
FIG. 4 is an exploded view of a catheter hub constructed in accordance with the invention.
Figure 5:
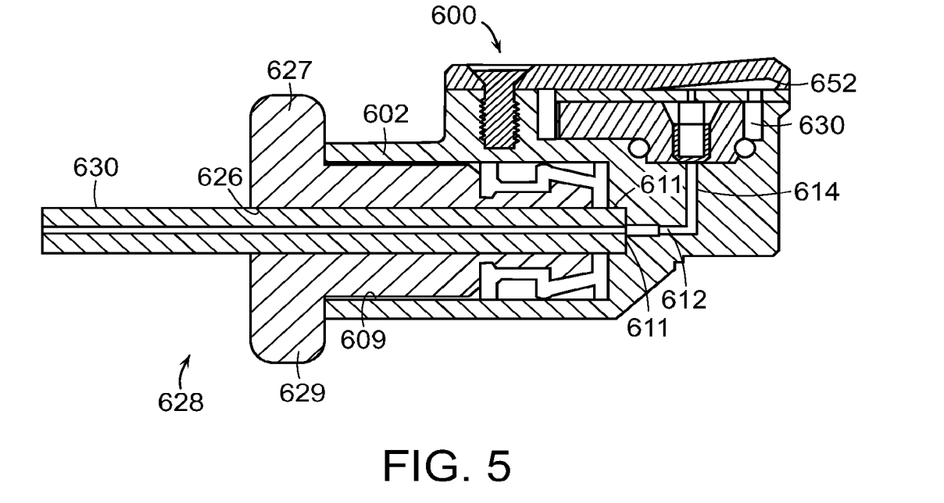
FIG. 5 is a sectional view of the catheter hub taken along line 5-5 of FIG. 6.
Figure 6:
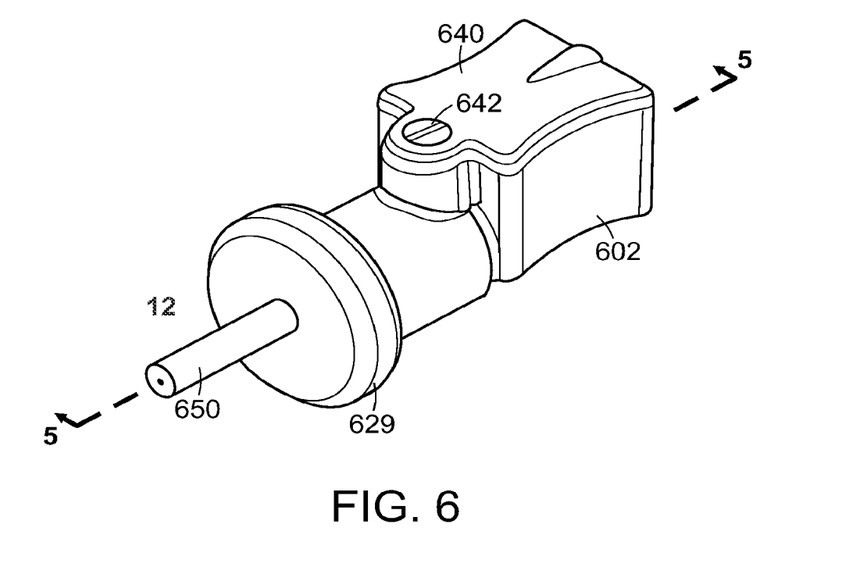
FIG. 6 is a perspective view of a catheter hub constructed in accordance with the invention.

Reference is now made to FIGS. 4-6 in which a charging system for an open catheter system constructed in accordance with the invention is provided. A catheter hub assembly, generally indicated as 600 includes a main body 602 having a chamber 609 formed through a portion thereof. Chamber 609 is in fluid communication with a channel 612 at one end (FIG. 5) and opens to the ambient environment at the other.

A pressure transducer assembly 630, includes a base 634 and is sized to fit within and substantially seal an opening 604 in main body 602. Transducer assembly 630 extends from a substrate 632 into main body 602 and holds a pressure transducer 636 in fluid communication with channel 612 through a second channel 614. A transducer lid 640 is affixed to main body 602 utilizing a fixing screw 642 to retain transducer assembly 630 in place within opening 604. Transducer assembly 630 includes electronic circuitry 638 such as touch pad connectors formed on substrate 632. Electronic circuitry 638 forms a circuit with transducer 636 as known in the art and electronically communicates through wires (not shown) to electronic circuitry for processing a transducer pressure signal.

A stopper assembly 622 is received within a bore formed at one end of chamber 609, as will be discussed in greater detail below to charge the catheter system. Stopper assembly 622 includes a push-in stopper 624 having an axial bore 626 extending through the entire length of push-in stopper 624. An axial bore 626 extends through the entire length of push-in stopper 624. A rubber seal 628 is disposed about a proximal end (facing hub assembly main body 602) in a preferred non-limiting embodiment is held in place by a tension fit. Catheter 650 is secured within axial bore 626 and extends at least through the entire length of axial bore 626 and push-in stopper 624. In a preferred embodiment, catheter 650 extends slightly beyond push-in stopper 624. Catheter 650 is affixed within push-in stopper by tension fit, sonic weld, adhesive or the like.

In an embodiment in which catheter 650 extends beyond push-in stopper 624, chamber 609 is formed with a chamfered channel 611 which is in fluid communication with channel 612. Channel 611 is sized to receive the extending end 652 of catheter 650.

In a preferred non-limiting embodiment, seal 628 has at least one section having an outer circumference which seals the interior of chamber 609. In at least one non-limiting preferred embodiment, seal 628 may have two or more concentric rings 628A, 628B, 628C, each of which has a diameter to seal the interior of chamber 609. However, it is equally within the scope of the invention to have an entire seal 628 of sufficient diameter along its length to seal chamber 609. In a preferred, but non-limiting embodiment, this seal 628 is made of rubber and therefore is pliant and can form the seal within chamber 609 through compression. However, any pliant restorative material such as a foam and some plastics capable of being restoratively compressed forming a substantially gas tight seal with the interior of chamber 609 may be used.

Stopper assembly 622 has a head 629 having a diameter greater than the remainder of stopper 622 and greater than the diameter of the entrance of chamber 609 which receives push-in stopper 624. In this way, when stopper assembly 622 is inserted into chamber 609, head 629 abuts against main body 602 preventing further insertion. In a preferred embodiment, the length from an interior surface 627 of head 629 to a front surface of the extending portion of catheter 650 is the same as the distance from channel 612 to the opening of chamber 609. In this way, inserting stopper assembly 622 into chamber 609 until interior surface 627 of head 629 contacts the entrance to chamber 609, places catheter 650 in fluid communication with channel 612 to seal catheter 650.

The dimension of rubber seal 628 forms a gas tight seal within chamber 609. Therefore, as stopper assembly 622 moves through chamber 609, stopper assembly 622 pushes a column of air within main body 602 ahead of stopper assembly 622. As the column of air fills channels 611 and 612 to a predetermined pressure, the remaining air is pushed into catheter 650 and charges the balloon about the distal end of catheter 650 to an initial setting. Because the volume of air within catheter hub assembly 600 is known, and fixed, the amount to which the balloon is inflated is fixed, and the starting pressure of the entire system is known.

The use of a stopper assembly 622 provides all of the benefits of the prior art syringe embodiment, for charging systems discussed above, with the added advantage of a simplified structure as the charging mechanism (the stopper assembly 622) is now constructed with the catheter as a single unit. Furthermore, by combining the transducer, and charging assembly with the catheter in this manner, the simplified structure allows for the catheters to be directly connected to the upstream electronics and even gang assembled to the upstream electronics.

Figure 7:
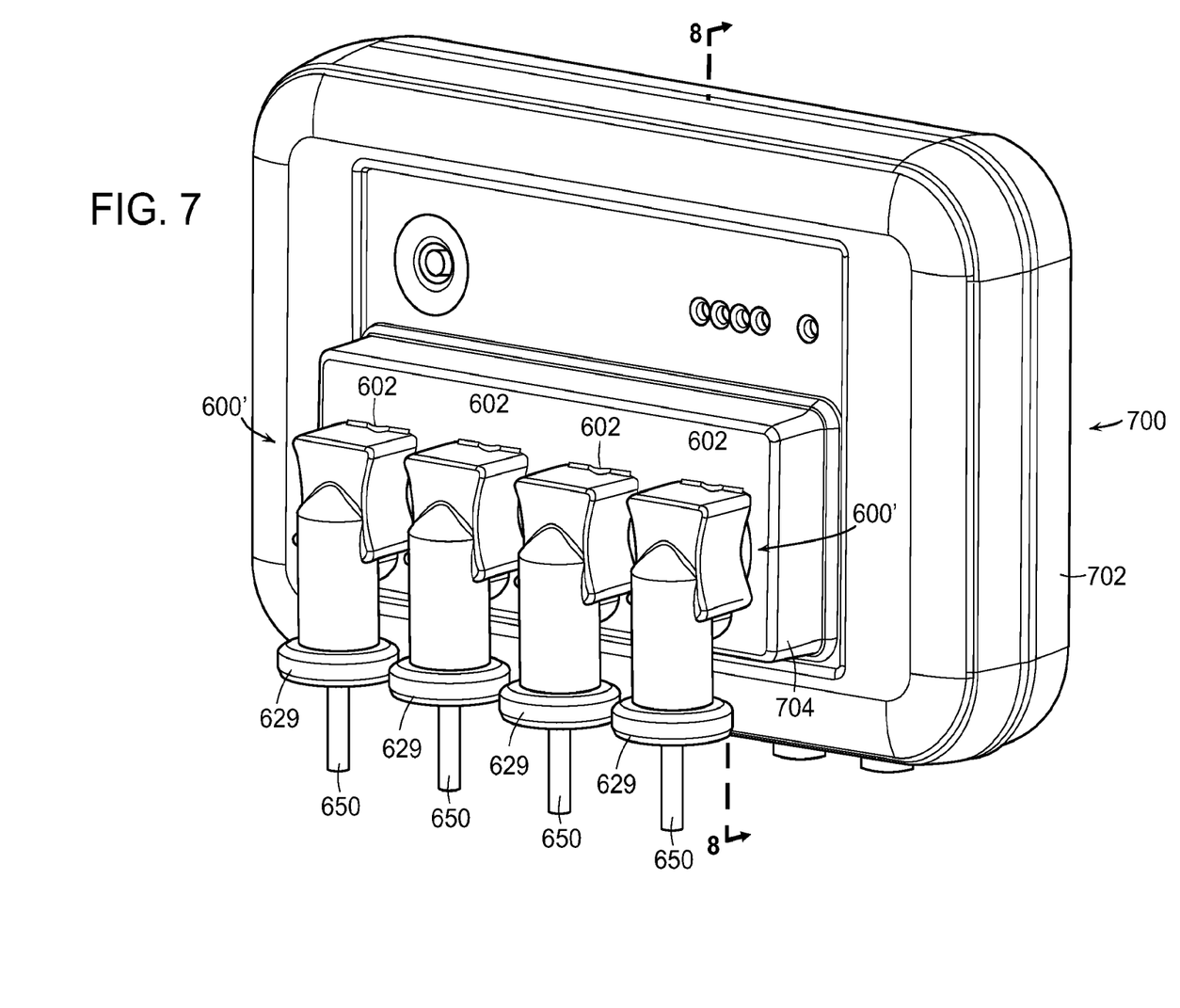
FIG. 7 is a perspective view of an electronic communication device constructed in accordance with the invention.
Figure 8:
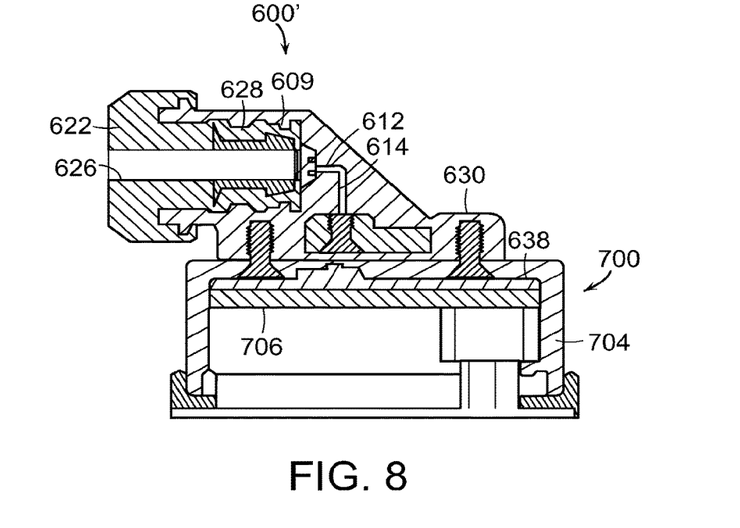
FIG. 8 is a sectional view taken along line 21-21 of FIG. 7.
Figure 9:
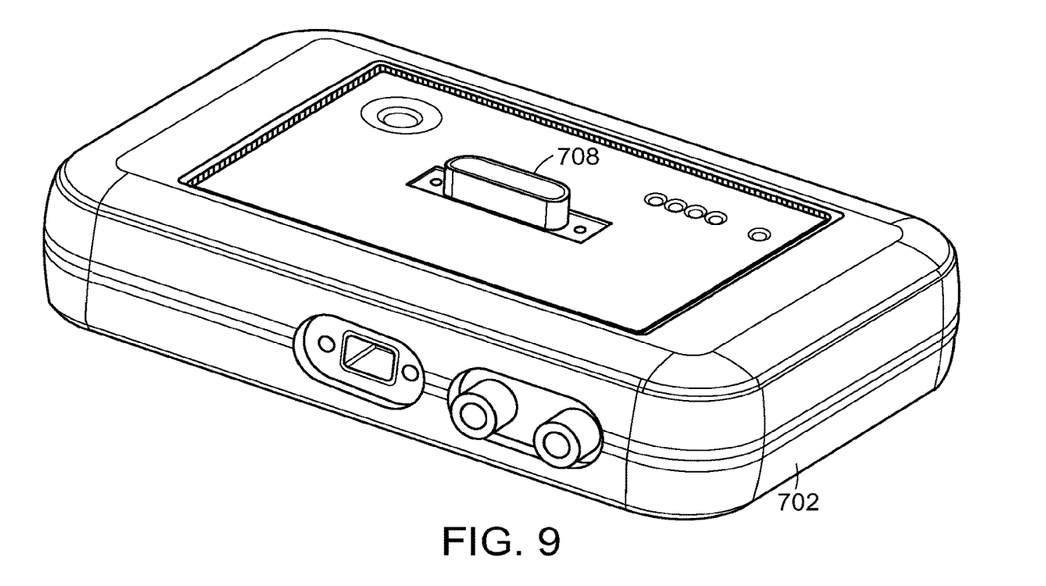
FIG. 9 is a perspective view of a circuitry housing in accordance with another embodiment of the invention.

Reference is made to FIGS. 7-9 in which an embodiment of the invention in which the stopper assembly embodiment are gang mounted as a pressure transducer array in communication with upstream electronic circuitry for operating upon the transducer signal. Like numerals are utilized to indicate like structure, the primary difference being the attachment of the catheter hub main body directly to the upstream electronics in a way that two or more catheters may be affixed to housing a main body housing assembly.

An electronics assembly 700 includes a housing 702. A connector 704 may be fixedly or selectively and removably affixed to housing 702. Both housing 702 and connector 704 include electronic circuitry for processing transducer signals. In one embodiment, connector 704 includes a circuit board 706 for directly communicating with touch pad 638 of transducer assembly 630. This circuit board may be as simple as a pass through communication interface or may form the signals for further processing. A second circuit board is contained within housing 702 and is in communication with the first circuit board 706 and may be as simple as a Bluetooth communication device to other upstream electronics such as a monitor and/or computer or may actually process the signals to be output directly to the monitor. In a preferred embodiment, communication between electronics assembly 700 and a monitor or a computer is done wirelessly such as Bluetooth communication, radio frequency communication, even cellular communication.

Two or more catheter hub assemblies 600', are affixed to housing 702. The catheter hub assembly 600' is identical to catheter hub assembly 600, the primary difference being that each housing 602 of catheter hub assembly 600' does not include a lid 640 or screw 642 so that the touch pad 638 or other circuitry and pressure transducer assembly 630 is exposed to the circuitry 706 within connector 704 for direct electrical connection. It follows that a plurality of stopper assemblies 622 are received within respective housing 602 and may be gang connected to circuitry in housing 702, reducing the number of connections to the computer and/or monitor.

In a preferred embodiment, electronics assembly 700 is modular. Each of catheter hub assembly 600' may be detachably connected to a connector 704 in a slide-on manner, a snap-on manner or some other affixing mechanism as known in the art. Similarly, connector 704 may be detachable from housing 702. As seen in FIG. 7, housing 702 may include an electrical connector 708 which is received by connector 704 to electrically connect the circuitry 706 within housing 702 to the circuitry within housing 702. Connector 704 is maintained on housing 702 by the friction fit between electrical connector 708 received within connector 704. We note that this embodiment, connector 708 is a male connector to be received by a female connector at connector 704. However, the male/female orientation may be easily reversed.

Figure 10:
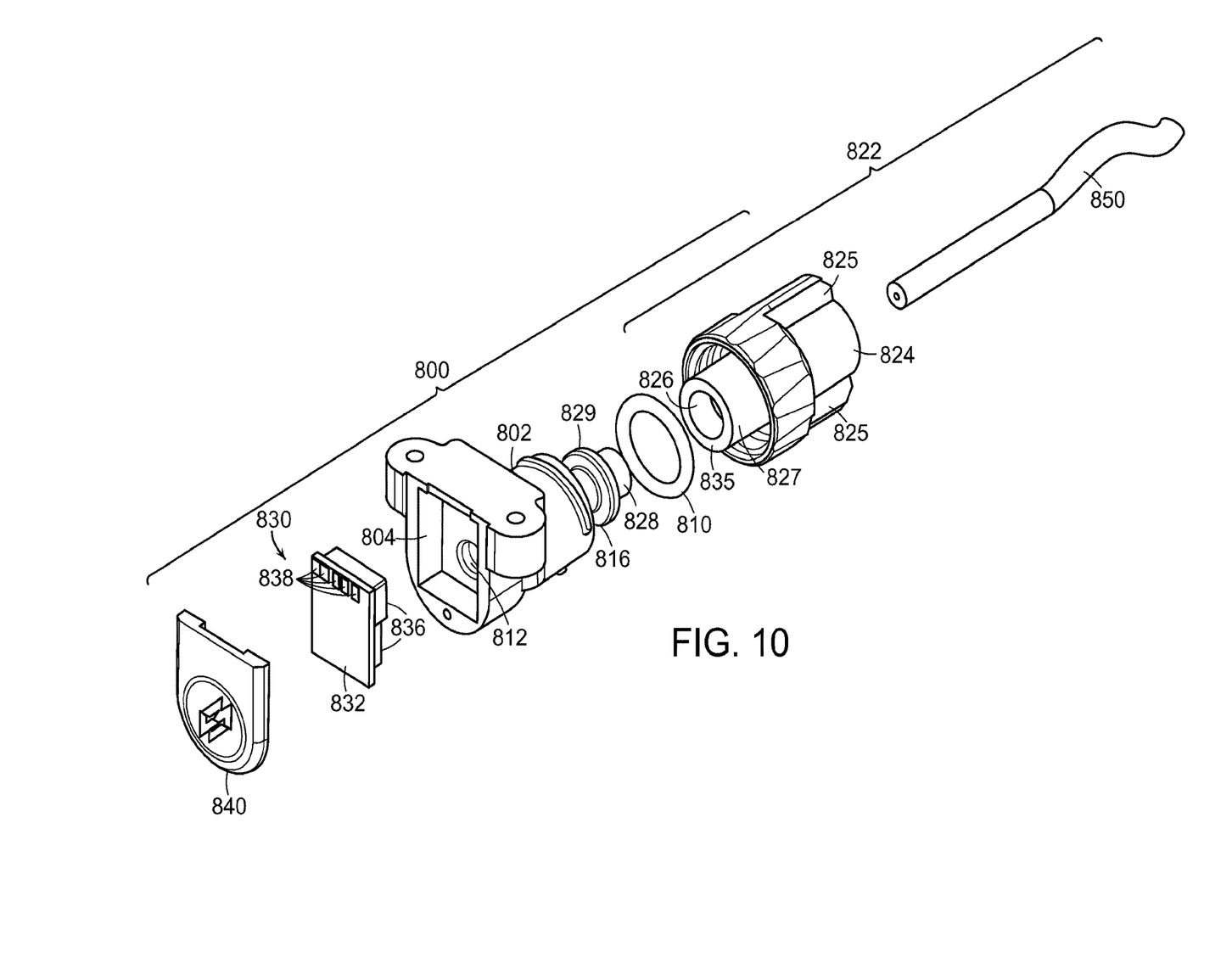
FIG. 10 is an exploded view of a catheter hub constructed in accordance with yet another embodiment of the invention.
Figure 11:
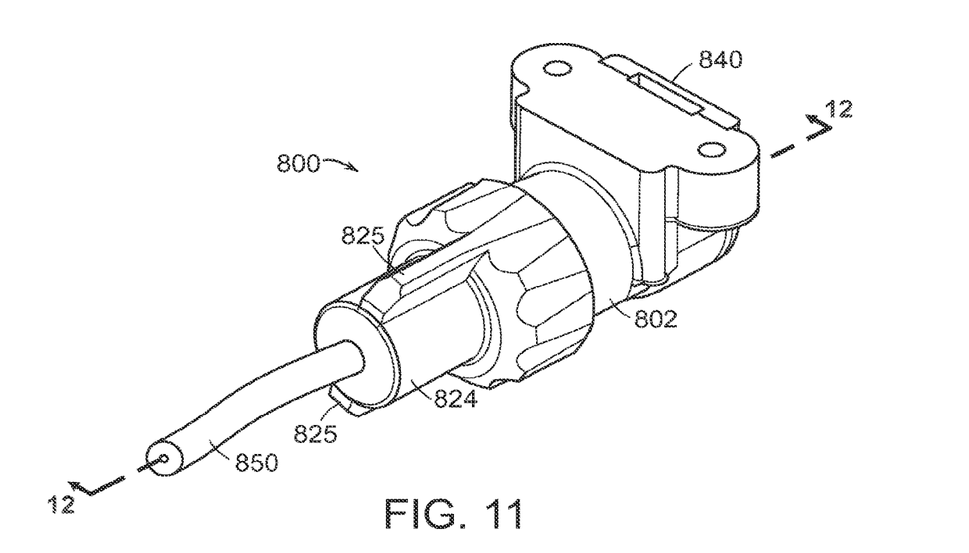
FIG. 11 is a perspective view of a catheter hub constructed in accordance with yet another embodiment of the invention.
Figure 12:
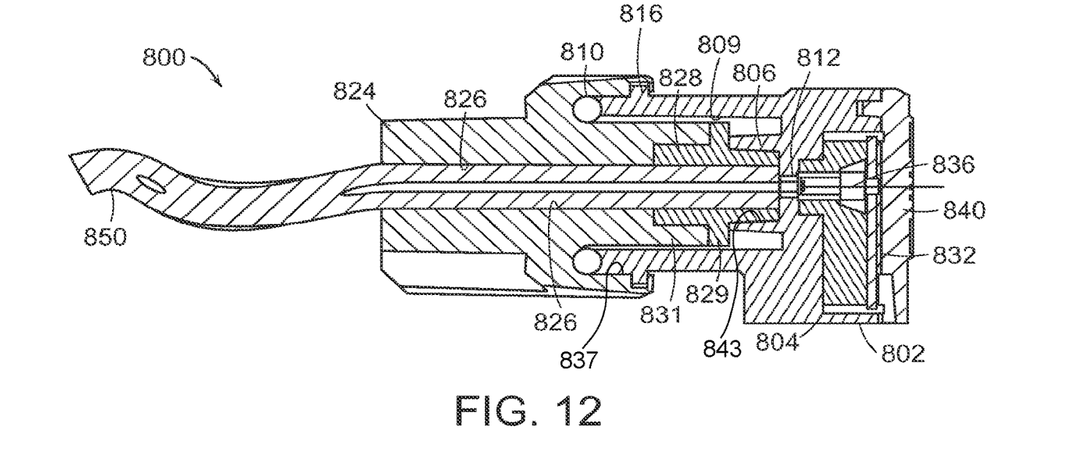
FIG. 12 is a sectional view of yet another catheter hub taken along line 12-12 of FIG. 12.

Reference is now made FIGS. 10-12 in which yet another embodiment of a catheter hub assembly constructed in accordance with the invention, generally indicated as 100 is provided. The primary differences between this embodiment and the embodiment of FIG. 4 are the use of a twist catheter stopper and the orientation of the transducer assembly relative to the housing body.

Catheter hub assembly 800 includes a main body 802 having a chamber 809 formed through a portion thereof. Chamber 809 includes a bore 843 in fluid communication with a channel 812 at one end (FIG. 12), and opens to the ambient environment at the other. Main body 802 includes a thread 816 mounted externally of that portion of housing 802 forming chamber 809.

A pressure transducer assembly 830 includes a substrate 832 sized to fit within and substantially seal an opening 804 in main body 802. A pressure transducer 836 is disposed on substrate 832 and is in fluid communication with channel 812. Transducer assembly 830 includes electronic circuitry 838 such as touchpad connectors formed on substrate 832. Electronic circuitry 838 forms a circuit with transducer 836 as known in the art and electronically communicates through wires (not shown) to electronic circuitry for processing a transducer pressure signal. A transducer lid 840 is affixed to main body 802 by clip-on or slip-on arrangement to retain transponder assembly 830 within opening 804.

A stopper assembly 822 receives a portion of main body 802 formed at the end of chamber 809 in fluid communication with the ambient atmosphere, as will be discussed in greater detail below, to charge the system. Stopper assembly 822 includes twist stopper 824 having grips 825 extending from an exterior surface thereof. A catheter 850 is secured within an axial bore 826 of twist stopper 824 and extends at least through the entire length of axial bore 826 and twist stopper 824. In a preferred embodiment, catheter 850 extends beyond twist stopper 824. Catheter 850 is affixed within stopper 824 by tension fit, sonic weld, adhesive or the like.

Stopper assembly 822 includes a bore member 831 having bore 826 extending therethrough. A recess 837 is formed about bore member 831 within twist stopper 824. Stopper assembly 822 includes resilient members to provide a seal between stopper assembly 822 and main body 802. First, a resilient 0-ring 810 is disposed within a recess 837 surrounding bore member 831. 0-ring 810 comes in contact with both main body 802 and the interior of catheter stopper 824 during charging as will be described below.

Secondly, when connected to body 802, a seal 828 sits within bore 826 of stopper 824 of chamber 809. Seal member 828 has a bore member 831 therethrough for receiving a portion of catheter 850 extending beyond twist stopper 824. A resilient member 829 extends about an outer surface of resilient seal 828 and acts as a positioner so that it is a distance along seal 828 to be flush against an end 835 of bore 826. During charging, a surface 806 within chamber 809 abuts resilient member 829 sealing the transition from bore 826 to bore 843, while member 829 seals bore 843 and bore member 831.

During use, stopper assembly 822 is inserted into chamber 809 until main body 802 is received within recess 837 of stopper 824 and abuts against 0-ring 810 sealing chamber 809 and preventing further insertion of main body 802. Thread 816 is received by a thread 827 within twist stopper 824 so that a slight twist utilizing grips 825 maintains twist stopper 824 on main body 802.

In a preferred embodiment, a portion of catheter 850 may abut against or extend into channel 812 when twist stopper 824 is sealed against main body 802. Bore member 831 extends into chamber 809. The housing for bore 826 forces resilient seal 828 against the interior space of main body 802 within chamber 809 to form a sealed fluid pathway including bore 826, bore 843 and channel 812. The relative dimensions with catheter 850 being disposed within the channels are set for catheter 850 to come in facing abutting relationship with channel 812 when twist stopper 824 is sealed against main body 802. In a preferred embodiment, a portion of catheter 850 may extend beyond resilient seal 828 into channel 812, so that catheter 850 is in fluid communication with channel 812 to seal catheter 850.

Resilient member 829 of seal 828 and 0-ring 810 form a gas tight seal within chamber 809. Therefore, as stopper assembly 822 moves through chamber 809, stopper assembly 822 pushes a column of air within main body 802 ahead of stopper assembly 822. As the column of air fills channels 812 to a predetermined pressure, the remaining air is pushed into catheter 850 and charges the balloon about the distal end of catheter 850 until set. Because the volume of chamber 809 of the catheter hub assembly 800 is known, and fixed, the amount to which the balloon is inflated is fixed and the starting pressure of the entire system is known.

Figure 13:
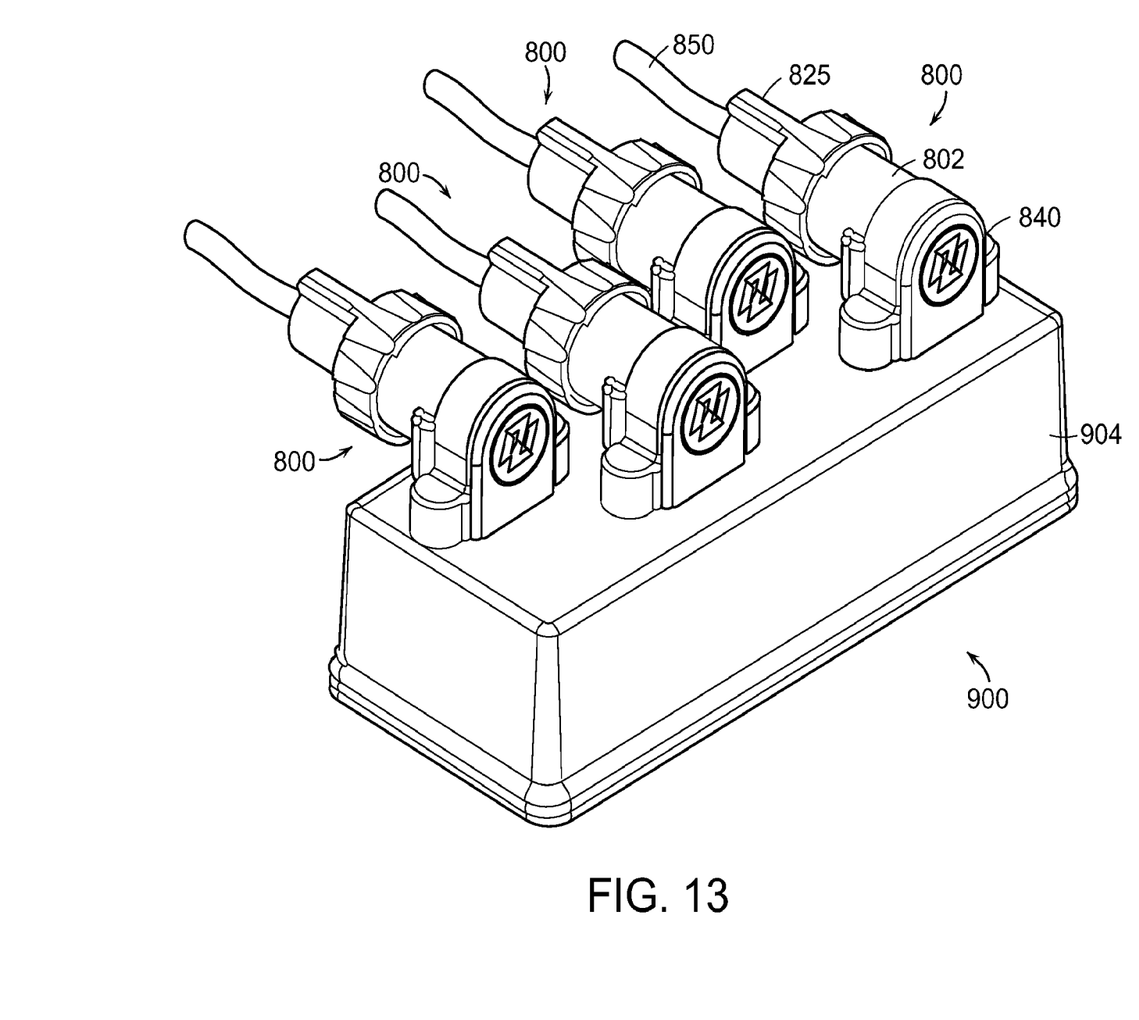
FIG. 13 is a perspective of an electronic communication device constructed in accordance with the invention.

Reference is now made to FIG. 13, which illustrates an electronic communication device 900 that includes a connector 904 for operating with housing 702 in accordance with another embodiment of the invention is provided. It is understood from the description above with respect to connector 704, that connector 904 includes a circuit board for directly communicating with electronic circuitry 838 of transducer assembly 830. The circuit board may be as simple as a pass-through communication interface or may form the signals for further processing. It communicates with other circuitry within housing 702 discussed above. The primary difference being the orientation of the circuitry to the catheter and connector 904 to form catheter hub assembly 800 affixed to the housing of connector 904. Two or more stopper assemblies 822 are received within respective housings 802 and may be gang connected to circuitry within housing 702 reducing the number of connections to a computer and monitor. The primary difference is the orientation of the transducer assembly 830 relative of the catheter and the circuitry within the housing of connector 904 (substantially right angles to each).

With the above embodiment, a simple closed catheter system is provided utilizing the ambient air during assembly.

It should be noted, that catheter hub assembly 600 may be used in either a closed fluid system or an open system in which there are no membranes about the eyelets as known in the art.

While this invention has been particularly shown and described to reference the preferred embodiments thereof, it would be understood by those skilled in the art that various changes in form and detail may be made therein without departing from the scope of the invention encompassed by the appended claims.

What is claimed as new and desired to be protected by Letters Patent of the United States is:

1. An electronics assembly for a catheter comprising:
    a housing;
    a first circuitry disposed within said housing;
    a connector housing disposed on, and configured to be detached and reattached to, an outer surface of said housing, said connector housing housing therein a second circuitry, the second circuitry communicating with the first circuitry when said connecter housing is attached to said housing;
    a first catheter hub assembly having a first catheter hub assembly housing, a first catheter at least partially disposed within said first catheter hub assembly housing, a first pressure sensor disposed within said first catheter hub assembly housing to sense a first pressure within the first catheter, the first catheter hub assembly housing having a chamber formed therein, the chamber having a predetermined volume, the first pressure sensor being disposed within the first catheter hub assembly, and the first catheter hub assembly being configured to be detached and reattached to an outer surface of the connector housing, wherein a second pressure sensor is configured to be in communication with said second circuitry when said first catheter hub assembly is attached to the housing;
    and at least a second catheter hub assembly having a second catheter hub assembly housing, a second catheter at least partially disposed within said second catheter hub assembly housing, a second pressure sensor disposed within the second catheter hub assembly housing to sense a pressure within the second catheter hub assembly housing, the second catheter hub assembly housing having a second chamber formed therein, the chamber having a second predetermined volume,
    wherein the second pressure sensor is disposed within the second catheter hub assembly, wherein the second catheter hub assembly is configured to be detached and reattached to an outer surface of the connector housing, wherein the second pressure sensor is configured to be in communication with the second circuitry when said second catheter hub assembly is attached to the housing;
    wherein each of the first catheter hub assembly and the second catheter hub assembly further comprise a stopper assembly comprising a bore formed within the stopper assembly, a seal disposed at least partially within said bore, and extending beyond said bore;
    the bore selectively connecting with at least one of the first catheter hub assembly and the at least second catheter hub assembly.

2. The electronics assembly of claim 1, wherein each of the first catheter and second catheter is disposed within a respective bore and along a length of said stopper assembly and said seal.

3. The catheter hub assembly of claim 1, wherein each respective seal includes a resilient member disposed between the bore in the respective catheter hub assembly, and the stopper assembly.

* * * * *